United States Patent
Lu

(12) 
(10) Patent No.: US 7,534,740 B2
(45) Date of Patent: May 19, 2009

(54) METHOD TO PRODUCE PHOTO-CATALYST PHYSICAL WATER MOLECULE FOR MEDICAL PURPOSES

(76) Inventor: Tsai-Chuan Lu, No. 560, Dong Yi Rd., Chia Yi City (TW)

( * ) Notice: Subject to any disclaimer, the term of this patent is extended or adjusted under 35 U.S.C. 154(b) by 442 days.

(21) Appl. No.: 11/459,630

(22) Filed: Jul. 24, 2006

(65) Prior Publication Data

US 2006/0258533 A1 Nov. 16, 2006

Related U.S. Application Data

(63) Continuation-in-part of application No. 10/943,889, filed on Sep. 20, 2004, now abandoned.

(51) Int. Cl.
*B01J 23/00* (2006.01)
*C01G 23/047* (2006.01)

(52) U.S. Cl. ................ 502/300; 502/350; 423/609; 423/610; 241/15; 241/17; 241/21; 424/604; 424/617; 422/22; 422/28; 604/20; 516/90

(58) Field of Classification Search .......... 423/608, 423/610; 502/350, 300; 604/20; 516/90; 214/15, 17, 21; 424/604, 617; 422/22, 28
See application file for complete search history.

(56) References Cited

U.S. PATENT DOCUMENTS 6,517,804 B1 * 2/2003 Kim et al. ............. 423/610

* cited by examiner

*Primary Examiner*—Vickie Kim
*Assistant Examiner*—Joseph V Micali
(74) *Attorney, Agent, or Firm*—WPAT, P.C.; Anthony King

(57) ABSTRACT

A method to produce photo-catalyst physical water molecule for medical purposes includes the following steps: mixing aqua pura and $TiO_2$ at the ratio of 1:1 at a temperature range of 50 to 60° C. to be ground and refrigerated in flasks of a first semi-product; adding aqua pura at the ratio of 1:1 and mixing well to become a second semi-product; diluting with aqua pura and mixing well to indicate a viscosity of 800 to 10000 centipoises; storing the solution in a sealed and transparent container to undergo photosynthesis for 24 hours at a temperature range of 40 to 50° C.; ridding off 1% suspension and foreign matters and impurities of the sediments to avail solution of 20% solid containment; finally diluting with approximately 100% aqua pura to 0.3 to 0.8%.

2 Claims, No Drawings

METHOD TO PRODUCE PHOTO-CATALYST PHYSICAL WATER MOLECULE FOR MEDICAL PURPOSES

This application is a continuation-in-part of my application filed Sep. 20, 2004, Ser. No. 10/943,889 now abandoned.

BACKGROUND OF THE INVENTION (a) Field of the Invention

The present invention relates to a method to produce photo-catalyst physical water molecule for medical purposes, and more particularly, to a method that has repeatedly ground aqua pura and $TiO_2$ into fine grains and well mixed, then stored with photosynthesis, condensed, filtered, and diluted with approximately 100% aqua pura into 0.3% to 0.8% solution for human body purification and clean environment including medical, environmental protection, sterilization, and anti-fungus purposes.

(b) Description of the Prior Art

Conventional photo-catalyst is usually prepared by $TiO_2$ in nanometer size and chemical adhesive. However, when organic epoxy adhesive is added, insufficient amount of the additive will burst the powder, and excessive amount of additive fails the results expected since toxic gas is prevented from conversion. When inorganic epoxy adhesive is added, insufficient amount of the additive fails adhesion, and excessive amount of the additive results in excessive burst metal powder.

The photo-catalyst added with chemical adhesion of the prior art is successful in air cleaning, sterilization and deodorizing applications at a place of ambient temperature ranging 35 to 40° C.; however, when the temperature of the photo-catalyst rises to 70° C. or higher, it gets more active to degrade the chemical adhesion. Consequently, the nanometer grains burst and the adhesion becomes brittle to cause serious contamination. Since they are so too small to be discharged by digestion duct, these burst grains when inhaled by human body will settled down in the lungs and cause permanent damage. Things could get worse if the additive relates to alcohol or chemical agent.

SUMMARY OF THE INVENTION

The primary purpose of the present invention is a method to produce photo-catalyst physical water molecule for human body purification and clean environment purposes including various medical, environmental, sterilization, and anti-fungus application. To achieve the purpose, aqua pura and $TiO_2$ are mixed at a ratio of 1:1, ground, refrigerated, and processed into flakes of a first semi-product; the first semi-product is then mixed well with aqua pura also at the ratio of 1:1 and ground into a second semi-product; and the second semi-product is further diluted with aqua pura at the ratio of 1:1 and mixed well to indicate a viscosity of 800 to 10000 centipoises then sealed and stored to undergo photosynthesis for 24 hours at a temperature range of 40 to 50° C. to be exposed to radiation for the impurities to settle down and filtered into a solution with 20% solid containment. Finally, 1% suspension, and foreign matters and impurities of the sediments are removed before being diluted with approximately 100% aqua pura into 0.3% to 0.8% concentration and well mixed to become the nanometer water molecule photo-catalyst. The present invention for not adding into any organic or inorganic adhesion eliminates the defective of burst grains due to the improper amount of added adhesion as found with the prior art.

DETAILED DESCRIPTION OF THE PREFERRED EMBODIMENTS

Photo-catalyst physical water molecule for medical purposes according to the present invention is prepared by having mixed aqua pura and $TiO_2$ at the ratio of 1:1 at a temperature range of 50 to 60° C., fine ground, refrigerated and processed into flakes of a first semi-product. The first semi-product is added with aqua pura at the ratio of 1:1 and well mixed, ground into a second semi-product. The second semi-product is diluted with aqua pura at the ratio of 1:1 to indicate a viscosity of 800 to 10000 centipoises and well mixed, sealed in a transparent bucket and stored to undergo photosynthesis for 24 hours at a temperature range of 40 to 50° C. and exposed to radiation to settle down impurities, then filtered to become a solution with 20% solid containment. 1% suspension and the impurities and foreign matters in the sediments are removed before adding approximately 100% aqua pura to be diluted to a concentration of 0.3 to 0.8%. The solution is finally well mixed to become photo-catalyst physical water molecule for medical purposes.

In the production of the present invention, the following materials and equipment are required:

1. $TiO_2$: must be pure, crystal like, strict white without contamination, free of foreign materials, free of chemical compounds, excellent process quality for fine grinding, electricity bearing, with a grain size averaged below 3000 nanometers.

2. Aqua pura: must be pure, free of other minerals, free of organics, free of additives, free of ferrous substance.

3. Container for process: must be fine and smooth, sealed with a lid, dual-layer of cooling and heating.

4. Production site: air conditioned, clean, equipped with temperature controlled room, light controlled room, kept at a constant ambient temperature of 20° C.

5. Mechanical equipment: must be clean, rinsed before production to make sure of keeping clean, free of foreign matters; rinsed again after production without leaving any residuals.

6. Test and inspection instruments: must be kept clean, rinsed to clean immediately after use, no foreign matter is allowed near the instrument.

7. Operators: only those who known for keeping good personal sanitary habit shall be assigned to the process.

The method to produce photo-catalyst physical water molecule for medical purposes comprises the following steps:

1. mixing and grinding aqua pura and $TiO_2$ at the ratio of 1:1 for 48 hours at a temperature range of 50 to 60° C. given with a test once each at the $24^{th}$ and the $48^{th}$ hours to such extent that the grain size profile shall be of 100 to 1000 nanometers and at a viscosity of 30000 centipoises;

2. lowering the temperature of the solution down to 0 to 20° C. in paste and freezing for 24 hours, and processing the iced paste into flakes of a first semi-product;

3. adding aqua pura at the ratio of 1:1 into the first semi-product, and mixing well the solution and grinding the mixture for 72 hours with a test run each at the $24^{th}$, the $48^{th}$, and the $72^{nd}$ hours to such extent with the grain size profile under 100 nanometers into paste status of a second semi-product at the viscosity of 1500 centipoises;

4. diluting the second semi-product with aqua pura at the ratio of 1:1 for the solution to indicate a viscosity of 800 to 10000 centipoises, then mixing well the solution to be ground into flattened grains in a size under 30 nanometers for 24 hours with a test run every 8 hours until the fineness, shape, electromagnet, settlement, viscosity, and crystal brightness meeting the consistence standard in three tests;

5. storing the solution in the sealed, transparent bucket to undergo photosynthesis for 24 hours at a temperature range of 40 to 50° C., and being exposed to radiation to settle down impurities;

6. filtering the finished product of the $TiO_2$-water photo-catalyst high concentration solution with 20% of solid containment and refined reactants cleaned and purified; 1% suspension and foreign matters and impurities of the sediments being rid off.

7. adding approximate 100% aqua pura to dilute the finish product into a concentration of 0.3 to 0.8% (e.g., 0.3%, 0.5%, 0.8%) and being well mixed.

As mentioned aforesaid, the photo-catalyst physical water molecule produced according to the present invention can be applied in human body purification and environment purification including medical, environmental protection, sterilization, and anti-fungus purposes.

1. Powdered Chinese cypress, Chinese herbal, and vanilla are added into the present invention to be dehydrated and well mixed in a pressurized vacuum vessel to force photo-catalyst physical water molecule into capillary fiber of the powder before packed into an air permeable fabric sachet.

2. The fabric sachet may be in a form of hanging bag, pillow, jacket pocket, thin sheet (to be adhered to a chair or on a bed), and placed in the car, at home or in the office to deodorize, sterilize, dehumidify, clean the air, and emit fragrance for curing and refreshing purposes when exposed to light or sunshine. Furthermore, when the sachet is applied in a pillow or sheet to contact the human skin for fending off fungus, help cure skin diseases; or when the sachet is dipped in water, it help purify water quality, skin care, and cure skin diseases.

Thus, specific embodiments and applications of method to produce photo-catalyst physical water molecule for medical purposes have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method to produce a photo-catalyst physical water molecule for medical purposes, comprising the following steps:
    a. mixing and grinding aqua pura and $TiO_2$ at the ratio of 1:1 for 48 hours at a temperature range of 50 to 60° C. given with a test once each at the $24^{th}$ and the $48^{th}$ hours to such extent that the grain size profile shall be of 100 to 1000 nanometers and a viscosity of 30000 centipoises;
    b. lowering the temperature of the solution down to 0 to 20° C. in paste and freezing for 24 hours, and processing the iced paste into flakes of a first semi-product;
    c. adding aqua pura at the ratio of 1:1 into the first semi-product and mixing well the solution and grinding the mixture for 72 hours with a test run each at the $24^{th}$, the $48^{th}$, and the $72^{nd}$ hours to such extent with the grain size profile under 100 nanometers into paste status of a second semi-product at a viscosity of 1500 centipoises;
    d. diluting the second semi-product with aqua pura at the ratio of 1:1 for the solution to indicate a viscosity of 800 to 10000 centipoises, then mixing well the solution to be ground into flattened grains in a size under 30 nanometers for 24 hours with a test run every 8 hours until the fineness, shape, electromagnet, settlement, viscosity, and crystal brightness meeting the consistence standard in three tests;
    e. storing the solution in a sealed, transparent bucket to undergo photosynthesis for 24 hours at a temperature range of 40 to 50° C., and being exposed to radiation to settle down impurities;
    f. filtering the finished product of the $TiO_2$—water photo-catalyst high concentration solution with 20% of solid containment and refined reactants cleaned and purified; 1% suspension and foreign matters and impurities of the sediments being rid off; and
    g. adding approximate 100% aqua pura to dilute the finish product into a concentration of 0.3 to 0.8% and being well mixed.

2. The method to produce photo-catalyst physical water molecule for medical purposes of claim 1, wherein $TiO_2$ is pure, crystal, strict white without contamination, free of foreign materials, free of chemical compounds, excellent process quality for fine grinding, electricity bearing, having an average grain size of below 3000 nanometers.

* * * * *